US006410019B1

United States Patent
De Simone et al.

(10) Patent No.: US 6,410,019 B1
(45) Date of Patent: *Jun. 25, 2002

(54) USE OF G CLASS IMMUNOGLOBULINS FOR THE TOPICAL TREATMENT OF ATOPIC DERMATITIS

(75) Inventors: Claudio De Simone, Ardea; Pietro Bruschi, Lissone, both of (IT)

(73) Assignee: Mendes s.u.r.l., Rome (IT)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/913,339

(22) PCT Filed: Mar. 12, 1996

(86) PCT No.: PCT/IT96/00047

§ 371 (c)(1),
(2), (4) Date: Sep. 11, 1997

(87) PCT Pub. No.: WO96/28186

PCT Pub. Date: Sep. 19, 1996

(30) Foreign Application Priority Data

Mar. 14, 1995 (IT) .................................. RM95A0154

(51) Int. Cl.⁷ ........................ A61K 39/395; C07K 16/00
(52) U.S. Cl. ............................. 424/130.1; 424/141.1; 430/387.1; 430/389.1; 430/868
(58) Field of Search ..................... 530/387.1, 389.1, 530/868; 424/130.1, 141.1

(56) References Cited

U.S. PATENT DOCUMENTS 5,141,742 A * 8/1992 Brown et al.
5,505,945 A * 4/1996 Gristina et al. .......... 424/164.1
5,530,102 A 6/1996 Gristina et al.
5,780,026 A * 7/1998 Yoshii et al. ............ 424/130.1

FOREIGN PATENT DOCUMENTS

EP 0 127 712 12/1984

OTHER PUBLICATIONS

Stedman's Medical Dictionary 24th Edition Williams and Wilkins pp. 380–381, 1982.*
Abe et al Cancer 68/6 1451–1459 Supple, 1991.*
Kimata, H., "High–dose intravenous gammaglobulin treatment for hyperimmunoglobulinemia E syndrome", Journal of Allergy and clinical Immunology, vol. 95, No. 3, pp. 771–774, Mar. 1995.*
Baird, K.A., "A new and effective treatment for psoriasis", Dermatologia Internationalis, vol. 4, No. 3, pp. 155–158, 1965.*
Meltzer, L., "Treatment of Cystic Acne with Gamma Globulin", Southern Medical Journal, vol. 54, pp. 85–86, Jan. 1961.*
Taddeucci–Brunelli et al, Treatment of atopic dermatitis in children (evaluation in the use of a hyposensibilitation therapy). Abstract, Ped. Med. Chir., vol. 8, No. 6, pp. 839–844, 1986.*
Kern, Arch Derm, 1962, vol. 85, pp. 623–624.*
Samitz and Pomerantz, A.M.A. ARch Derm, 1959, vol. 79, 641–643.*
Etheridge and Waddell, Virginia Med Monthly, 1960, vol. 87, pp. 623–624.*
Morel et al, Journal of Autoimmunity, 1992, vol. 5, pp. 465–477.*

* cited by examiner

Primary Examiner—Anthony C. Caputa
Assistant Examiner—Karen A. Canella
(74) Attorney, Agent, or Firm—Nixon & Vanderhye

(57) ABSTRACT

The use of G class immunoglobulins, particularly immunoglobulins for intravenous use or for intramuscular use to produce a medicine for the local therapeutic treatment of dermatitis, particularly acne, contact dermatitis, atopic dermatitis, eczema and ichthyosis, psoriasis, papulosquamous dermatopathies (seborrehic dermatitis, erythrodermia, etc.), as well as fungus, parasite, bacterium and virus infection dermatitis is disclosed. The pharmaceutical composition containing G class immunoglobulins suitable for topical application for the treatment of dermatitis is also disclosed.

4 Claims, No Drawings

USE OF G CLASS IMMUNOGLOBULINS FOR THE TOPICAL TREATMENT OF ATOPIC DERMATITIS

This application is a national stage filing of International Application number PCT/IT96/00047, filed Mar. 12,1996.

The present invention relates to a new therapeutic use of G class immunoglobulins, particularly immunoglobulins for intravenous use (IVIG) or for intramuscular use (IMIG). More particularly, the present invention relates to the topical use of G class immunoglobulins which are normally administered intravenously or intramuscularly for the therapeutic treatment of dermatitis, particularly acne, contact dermatitis, atopic dermatitis, eczema and ichthyosis, psoriasis, papulosquamous dermatopathies (seborrheic dermatitis, erythrodermia, etc.), as well as fungus, parasite, bacterium and virus infection dermatitis.

Therefore, this invention also relates to the pharmaceutical compositions suitable for topical application, which contain G class immunoglobulins, and particularly IVIG or IMIG, as the active ingredient.

As is well known, the term "immunoglobulins for intravenous use" indicates a human-protein-based product, at least 90% of which has the electrophoretic mobility of gammaglobulin (IgG), at least 90% of IgG being made up of monomer. Traces of IgA and IgM may also be present. The distribution of the IgG subclasses is similar to that encountered in normal serum.

Several commercial immunoglobulin preparations for intravenous use are currently available on the market, e.g. under the trade marks VENO-GLOBULIN®, GAMMIMUNE®, SANDOGLOBULIN®, GAMMAGARD®, GAMMAR® and IVEGAAM®.

The "immunoglobulins for intramuscular use" differ from the intravenous immunoglobulins in their lower degree of purity. Various commercial preparations of immunoglobulins for intramuscular use are currently available on the market, e.g. under the trade marks GLOBUMAN®, GAMMABULINE®, LIOGAMMA®, BOEHRIGAMMA® and UMANGAMMA®.

The skin interacts continuously and intimately with a vast range of environmental agents more than any other organ in the body. The environment comes into contact with the body in the form of substances or forces (physical, chemical, biological) and via different routes: irradiation, air, food, direct contact with the skin, injections, or psychosocial interactions. All these agents may lead to diseases of the skin (Ring, J:, "The skin and the environment", Hautarzt, 44:625-35, 1993). Atopic dermatitis (AD) is a multifactorial skin disease with a chronic or chronic-recurrent course, which often sets in during infancy. The aetiology of this troublesome skin condition is still obscure, but an immunological disorder of the T cell immune response is likely involved in its pathogenesis (Wuthrich, B., Atopic dermatitis", Ther. Umsch., 51:45–54, 1994).

Recent discoveries have revealed various key factors in maintaining the vicious circle of AD, associated with elevated activation of T lymphocytes, hyper-stimulating Langerhans cells, an abnormal cell-mediated immunity and an overproduction of IgEs by the B cells (Cooper, KID., "Atopic dermatitis: recent trends in pathogenesis and therapy", J. Invest. Dermatol., 102:128–37, 1994). In-situ hybridization has revealed that, as compared to normal control skin or to the unaffected skin of AD sufferers, the acute and chronic lesions of the skin had a significantly greater numbers of cells which were positive for IL-4 and IL-5 mRNA (Hamid, Q., et al. "Differential in situ cytokine gene expression in acute versus chronic atopic dermatitis", J. Clin. Invest., 94:870–6, 1994). These and other data suggest the activation of a selected population of T-helper cells which produce a type of Th2 cytokines related to IL-4 and IL-5 but not to IL-2 and interferon-γ (IFN-γ) in AD (Kagi, M.K., et al, "Differential cytokine profiles in peripheral blood lymphocyte supernatants and skin biopsies from patients with different forms of atopic dermatitis, psoriasis and normal individuals", Int. Arch. Allergy Immunol., 103:332–40, 1994). The micro-organisms of the skin flora may also be a further stimulus for allergic reactions of the skin. Abnormal bacterial colonization of the skin is a typical characteristic of AD. Staphylococcus aureus (Staph. aureus) is the most common pathogen and in some cases an antimicrobial and antifungal treatment has proved useful (Ring, J., et al, "Atopic eczema: role of micro-organisms on the skin surface", Allergy, 47:265–9, 1992).

Conventional therapy remains the mainstay of treatment of atopic dermatitis, but often proves unsatisfactory. New therapies based on the concepts outlined above are being tested in clinical trials, and for this purpose trials have been suggested with modifiers of the biological response such as interferon-γ, cyclosporin A, or thymopentin, administered parenterally (Cooper, KD., "Atopic dermatitis: recent trends in pathogenesis and therapy", J. Invest. Dermatol., 102:128–37, 1994).

To date, the accepted use of IVIG and IMIG has been as antibody replacement in states of immunodeficiency to treat and/or prevent infectious diseases (Newland A.C., "The use and mechanism of action of intravenous immunoglobulin", Br. J. Haematol., 72:301–5, 1989). In addition, there is increasing evidence that intravenous infusion of large amounts of polymeric immunoglobulin causes more than simple antibody replacement and may have a profound effect on the reticulendothelial system. IVIG and IMIG can alter the function of B and T lymphocytes and cause short-term blockade of phagocyte function with down-regulation of immunological activity (Newland, A.C., Macey et al, "Intravenous immunoglobulin: mechanism of action and their clinical application" in "Immunotherapy with intravenous immunoglobulins", edited by P. Imbrach, Academic Press, London, 1991, pp. 14–25). It is conceptually important to note that, in numerous diseases, more than one mechanism of action is possible and that the therapeutic effect may be due to several concomitant actions rather than to any single mechanism. Nevertheless, the IVIG and IMIG preparations have been developed to date so as to allow systemic administration.

As regards skin diseases, an improvement in AD has been observed in patients suffering both from AD and from Kawasaki's disease or from idiopathic thrombocytopenia, but the immunoglobulins were administered, as usual, by the intravenous route and at high doses (Kimata, H., "High dose gammaglobulin treatment for atopic dermatitis", Arch. Dis. Child., 70:335–6, 1994).

Surprisingly, however, it has now been found that G class immunoglobulins, and in particular IVIGs or IMIGs, in solution or in the form of ointments or gels, or in liposomes (or other formulations) at concentrations of 0.1–25% are potentially effective for the prophylaxis and treatment of AD or of other skin diseases characterized by a poorly regulated immune response and/or by abnormal bacterial, viral or fungal colonization.

This efficacy of the immunoglobulins has been tested in various studies in man. Some of these studies will now be described here. The local administration of immunoglobulins at the doses indicated brings about remission of the inflammatory process without causing any toxic or unwanted side effects.

STUDIES IN MAN

Study No. 1

In this study we selected 8 patients suffering from acute AD in whom we studied blood levels of total lymphocytes as well as of CD3, CD4 and CD 8, and the CD4:CD8 ratio. These parameters were determined in two clinical phases, i.e. in the acute phase (pre-treatment) and in another phase in which the lesions regressed (post-treatment). IVIGs were administered topically in the form of a 25% solution. The IVIGs were applied to the skin lesions three times daily for a period of 14 days. The aim of this work was to study the changes in these lymphocyte subpopulations in each of the phases. We also studied a control group consisting of 8 healthy subjects so as to reinforce the results obtained. We found no significant difference between the results obtained in the two phases or as compared to the control group (Table 1). These data indicate that IVIGs when applied topically in the form of a 25% solution, do not modify the lymphocyte subpopulations in peripheral blood. Their therapeutic efficacy is thus attributable to a local effect.

TABLE 1

Absolute number of lymphocytes in peripheral blood: percentages of CD3, CD4 and CD8 cells and CD4:CD8 ratio.

|  | Lymphocytes | CD3 | CD4 | CD8 | CD4:CD8 | Statistics |
|---|---|---|---|---|---|---|
| Patients |  |  |  |  |  |  |
| Before | 1870 ± 324 | 67 ± 13 | 41 ± 8 | 27 ± 0 | 1.6 | ns |
| After | 1920 ± 376 | 72 ± 15 | 88 ± 6 | 16 ± 7 | 1.4 | ns |
| Controls |  |  |  |  |  |  |
| Before | 1903 ± 411 | 70 ± 12 | 49 ± 10 | 29 ± 9 | 1.4 | ns |
| After | 1928 ± 407 | 70 ± 8 | 40 ± 11 | 28 ± 8 | 1.4 | ns |

Study No. 2

In this study IVIGs were administered topically in the form of a 0,1% solution and applied to the skin lesions three times daily for a period of 14 days. A total of 6 patients with acute AD lesions were treated. No other type of treatment was allowed. We used in situ hybridization, as previously described (Hamid, Q., et al "Differential in situ cytoline gene expression in acute versus chronic atopic dermatitis", *J. Clin. Invest:*, 94:870–6, 1994) to examine the expression of the messenger RNA (MRNA) of interleukin 4 (IL-4) and interleukin 5 (IL-5) in skin biopsies. In comparison with pre-treatment the skin lesions were no longer present and a significantly lower number of cells positive for IL-4 ($P<0.01$) and IL-5 ($P<0.01$) mRNA were detected (Table 2). These data indicate that acute AD lesions are associated with an increased activation of the IL-4 and IL-5 genes, and that treatment with IVIGs is followed by a reduced expression of IL-4 and IL-5 at local level.

TABLE 2

Differential in situ cytokine gene expression in skin biopsies before and after treatment. Results are expressed as mean number of positive cells per high potency field (0.202 mm$^2$)

|  | Pre-treatment | Post-treatment | Statistics |
|---|---|---|---|
| IL-4 mRNA | 22 ± 4 | 4 ± 2 | P < 0.01 |
| IL-5 mRNA | 14 ± 5 | 2 ± 1 | P < 0.01 |

Study No. 3

In this study we assessed the expression of Th1-like cytokine and interferon-γ in three patients suffering from AD in whom a Staph. aureus superinfection had been observed clinically and confirmed microbiologically by skin biopsy culture. In comparison with normal skin (3 volunteers), the expression of interferon-γ increased in the AD lesions. After treatment with IVIG in the form of a 5% suspension 4 times daily for 16 days, the lesions disappeared and the increased expression of interferon-γ MRNA proved to be significantly down controlled (Table 3). These data indicate that the thera-peutic efficacy of WIGs is associated with a reduced colonization by micro-organisms and with modulation of interferon-γ mRNA expression.

TABLE 3

Differential in situ interferon-γ gene expression in skin biopsies before and after treatment in patients and controls. Results are expressed as mean number of positive cells per high potency field (0.202 mm$^2$)

|  | Pre-treatment | Post-treatment | Statistics |
|---|---|---|---|
| Patients | 30 ± 6 | 14 ± 5 | P < 0.02 |
| Control | 7 ± 3 | 8 ± 5 | ns |

The compositions of the invention (solutions, ointments, creams gels, liposomes, etc.) can be prepared using conventional techniques and excipients, e.g. as described in "Remington's Pharmaceutical Sciences Handbook", Mack Pub. Co., New York, USA, XVIII Ed., 1984, as will be self-evident to any person skilled in the art.

In addition to suitable excipients, these compositions may also contain antibiotics, antiviral agents, antifungal agents, vitamins, anti-inflammatory agents, antipruritics and/or antimicrobials, unsaturated fatty acids and immunosuppressive agents.

What is claimed is:

1. A method of treating the lesions of atopic dermatitis comprising topically administering to the atopic dermatitis lesions of a patient in need thereof an amount of G class immunoglobulin effective to treat the dermatitis and continuing topical application until the lesions disappear.

2. The method of claim 1 in which the G class immunoglobulin is in a topically applied solution, ointment, cream, gel or liposome.

3. The method of claim 1 in which in addition to the G class immunoglobulin also applied is an antibiotic agent, an antiviral agent, an antifungal agent, a vitamin, an anti-inflammatory, an antipyuretic, an antimicrobial, an usaturated fatty acid or an immunosuppressive agent.

4. The method of claim 1 in which a composition is topically applied in which the G class immunoglobulin is present in a concentration of from 0.1 to 25%.

* * * * *